US012558039B2

(12) United States Patent
Mountford et al.

(10) Patent No.: US 12,558,039 B2
(45) Date of Patent: Feb. 24, 2026

(54) METHOD AND SYSTEM FOR ACQUIRING SPECTRAL DATA FOR USE IN ASSESSING RISK OF BREAST CANCER

(71) Applicant: DatChem, Brisbane City (AU)

(72) Inventors: Carolyn Mountford, Ryde (AU); Gorane Santamaria, Bowen Hills (AU); Peter Malycha, St Georges (AU); Natali Naude, Ninderry (AU)

( * ) Notice: Subject to any disclaimer, the term of this patent is extended or adjusted under 35 U.S.C. 154(b) by 0 days.

(21) Appl. No.: 17/566,182

(22) Filed: Dec. 30, 2021

(65) Prior Publication Data

US 2022/0202374 A1    Jun. 30, 2022

Related U.S. Application Data

(60) Provisional application No. 63/131,894, filed on Dec. 30, 2020.

(51) Int. Cl.
*A61B 5/00*         (2006.01)
*A61B 5/055*        (2006.01)

(52) U.S. Cl.
CPC ............ *A61B 5/7275* (2013.01); *A61B 5/004* (2013.01); *A61B 5/055* (2013.01)

(58) Field of Classification Search
None
See application file for complete search history.

(56) References Cited

U.S. PATENT DOCUMENTS

2016/0022197 A1    1/2016  Ramadan et al.
2020/0217912 A1    7/2020  Mountford

FOREIGN PATENT DOCUMENTS

EP         1848333 B1 * 10/2013  ............. A61B 5/055

OTHER PUBLICATIONS

Mallikourti et al., "Phased-array combination of 2D MRS for lipid composition quantification in patients with breast cancer," (Nov. 18, 2020), Sci Rep 10, 20041 (2020). (Year: 2020).*
Cheng et al., "The Value of 1H-MRS and MRI in Combined Methylmalonic Aciduria and Homocystinuria," (Feb. 28, 2019), J Comput Assist Tomogr. Jul.-Aug. 2019; 43(4): 559-562. (Year: 2019).*
Van der Graaf, "In vivo magnetic resonance spectroscopy: basic methodology and clinical applications," (Aug. 13, 2009), Eur Biophys J (2010) 39:527-540. (Year: 2009).*

(Continued)

*Primary Examiner* — Keith M Raymond
*Assistant Examiner* — Ashish S Jasani
(74) *Attorney, Agent, or Firm* — Lucas & Mercanti, LLP

(57)         ABSTRACT
A method and system enabling a determination of the risk of developing breast cancer of a subject, comprises using a magnetic resonance spectroscopy device to obtain the level of the spectral signal at 3.15 and 3.19 ppm, within the breast tissue of the subject, and comparing the level of the spectral signal obtained in the first step with a reference level of a spectral signal at 3.15 and 3.19 ppm of the breast of a healthy subject, to determine whether the level of the signal obtained in the first step exceeds the reference level of a healthy subject is comparable to that of a subject known to be at elevated risk; or is elevated to the level of persons known to be carrying a gene mutation.

12 Claims, 4 Drawing Sheets

(56) References Cited

OTHER PUBLICATIONS

Notification of Transmittal of the International Search Report and the Written Opinion of the International Searching Authority, or the Declaration; PCT/IB2021/062503 filed Dec. 30, 2021; Mail Date: Feb. 7, 2022.

Written Opinion of the International Searching Authority; PCT/IB2021/062503 filed Dec. 30, 2021; Mail Date: Feb. 7, 2022.

Hauge, Ileana. Establishing a Method for Measuring Serum Methylmalonic Acid and Application to Women with a History of Breast Cancer. Published by Defense Technical Information Center on Jan. 1, 2002.

Gomes, A.P., Ilter, D., Low, V et al. Age-induced accumulation of methylmalonic acid promotes tumour progression. Nature 585, 283-287 (2020).

Domagoj Javor, et al., Automated analysis of the total choline resonance peak in breast proton magnetic resonance spectroscopy, NMR in Biomedicine, Feb. 2024, Article e5054, vol. 37, No. 2, Wiley, Hoboken, New Jersey, USA.

Peter Stanwell, Carolyn Mountford, In vivo proton MR spectroscopy of the breast, RadioGraphics, Oct. 2007 (Supplement), pp. S253-S266, vol. 27 (Suppl. Issue), Radiological Society of North America (RSNA), Oak Brook, Illinois, USA.

* cited by examiner

METHOD AND SYSTEM FOR ACQUIRING SPECTRAL DATA FOR USE IN ASSESSING RISK OF BREAST CANCER

TECHNICAL FIELD

The present invention is directed to a method and system for acquiring spectral data from breast tissue using magnetic resonance spectroscopy (MRS) which can be used to assess risk of breast cancer.

BACKGROUND OF THE INVENTION

Throughout this application various references are cited. They are incorporated by reference herein, to better understand the invention.

There is an important need in the healthcare field to reliably and easily assess a woman's risk of developing breast cancer. There are various ways that have been proposed for assessing the risk of breast cancer. One way is referred to as an IBIS (International Breast Cancer Intervention Study) score.

A recent paper by Gomes at al[1] linked Methylmalonic acid (MMA) with advancing age and a systemic environment that favours the progression and aggressiveness of tumours. The report suggests that MMA is upregulated in the serum of older people and functions as a mediator of tumour progression. Specifically, it demonstrated that MMA could induce the human transcription factor SOX4 expression and consequently elicit transcriptional reprogramming to give cancer cells aggressive properties. They also hypothesise that MMA may provide a therapeutic target. Methylmalonic acid (MMA or 2-methylpropanedioic acid), CH,CH(CO,H)(CO,H) is a dicarboxylic acid that is a C-methylated derivative of malonate. The MMA derivative is a vital intermediate in the metabolism of fat and protein and Methylmalonic acid metabolism.

While assigning MMA in cerebrospinal fluid in those with Vitamin $B_{12}$ deficiency, Commodari et al[2] demonstrated the pH sensitivity of MMA. At 400 MHz the proton MR spectrum has two multiplets centered at 1.23 and 3.17 ppm (parts per million) when recorded in D20 at 25 C and pH 7.2. The multiplets centered at 3.17[3] has four resonances at 3.14, 3.16, 3.17 and 3.18 ppm in the ratio of 1:4:4:1. (https://hmdb.ca/spectra/nmr_one_d/1183).

Epidemiological studies report breast density to be an independent risk factor for breast cancer[4-6]. Studies suggest that increased breast density makes a woman 4 to 6-fold more likely to develop breast cancer[7].

A recent study, by others, has shown that high levels of MMA, boost a tumour's malignancy allowing cancer cells to breach new tissues, fight off chemotherapies, and survive.

SUMMARY OF THE INVENTION

In accordance with the present invention, spectral data of woman's breast tissue has been obtained which enables an assessment of breast cancer depending on the presence of spectral resonances at 3.15 and 3.19 ppm, which are different from the resonances at 3.14, 3.16, 3.17, and 3.18 ppm reported in Commodari et al.). A tentative assignment of methylmalonic acid, or MMA, has been made for these spectral resonances in the breast tissue of apparently healthy women and those at elevated risk for breast cancer, using in vivo two-dimensional Correlated Spectroscopy (2D COSY) in a 3T clinical scanner. The resonances may be recorded and measured using a full 2D data set, a specific range of delays in the D COSY that encompass the strongest signal for the MMA, or by data mining a 1D MR spectrum REF Stanwell Neuroimage. The two resonances which have been recorded at 3.15 and 3.19 ppm from women known through other means to have an elevated risk of breast cancer, are consistent with the presence of the MMA molecule in breast tissue. In apparently healthy women, with no significant family history, those with highly dense breast tissue have significantly five times higher levels of MMA than those with low breast density. In those women with an apparently elevated risk of cancer, as judged by their IBIS score, the MMA is highest in those carrying the BRCA gene mutations. The level of the two resonances, recorded at 3.15 and 3.19 ppm, increase linearly with the risk of breast cancer as deduced by the IBIS risk score.

While undertaking a study to non-invasively monitor changes at a molecular level in an apparently healthy breast of those at risk for cancer and those with no known risk for cancer, using in vivo two-dimensional Localised COrrelated SpectroscopY (2D COSY), the assignment of MMA was possible. The levels of this molecule in these conditions may be compared with menopausal status and breast density and the IBIS score for risk of cancer.

The invention provides a method enabling a determination of the risk of developing breast cancer of a subject, comprising: using a magnetic resonance spectroscopy device to obtain the level of the spectral signal at 3.15 and 3.19 ppm, within the breast tissue of the subject, and comparing (i) the level of the spectral signal obtained with (ii) a reference level of a spectral signal at 3.15 and 3.19 ppm from the breast of a healthy subject, to determine whether (iii) the level of the signal obtained exceeds the reference level of a healthy subject (see top section of FIG. 4); (iv) is comparable to that of a subject known to be at elevated risk (see second section of FIG. 4); or (v) is elevated to the level of persons known to be carrying a gene mutation (see last two sections of FIG. 4).

The spectral signal at 3.15 and 3.19 ppm may be is that of methylmalonic acid (MMA). The spectral signal may be obtained using 2D COrelated SpectroscopY (2D COSY). The spectral signal may be obtained using data mining of a 1D MRS signal. The results may be compared to an International Breast cancer Intervention Study (IBIS) score of the subject.

The invention provides a system for enabling a determination of the risk of developing breast cancer of a subject, comprising: a magnetic resonance spectroscopy device to obtain the level of the spectral signal at 3.15 and 3.19 ppm, within the breast tissue of the subject, and a comparator for comparing (i) the level of the spectral signal obtained with (ii) a reference level of a spectral signal at 3.15 and 3.19 ppm from the breast of a healthy subject, to determine whether (iii) the level of the signal obtained exceeds the reference level of a healthy subject (see top section of FIG. 4), (iv) is comparable to that of a subject known to be at elevated risk (see second section of FIG. 4), or (v) is elevated to the level of persons known to be carrying a gene mutation (see last two sections of FIG. 4).

The spectral signal at 3.15 and 3.19 ppm may be that of methylmalonic acid (MMA). The spectral signal may be obtained using 2D COrelated SpectroscopY (2D COSY) or by datamining 1D MRS. The spectral signal may be obtained using data mining of a 1D MRS signal. The results may be compared to an International Breast cancer Intervention Study (IBIS) score of the subject.

The invention provides a method enabling a determination of the risk of developing breast cancer of a subject, comprising: processing spectral data obtained from breast tissue of the subject using a magnetic resonance spectroscopy device to obtain the level of the spectral signal at 3.15 and 3.19 ppm, and comparing the level of the spectral signal obtained with a reference level of a spectral signal at 3.15 and 3.19 ppm from the breast of a healthy subject, to determine whether the level of the signal obtained exceeds the reference level of a healthy subject; is comparable to that of a subject known to be at elevated risk; or is elevated to the level of persons known to be carrying a gene mutation.

The spectral signal at 3.15 and 3.19 ppm may be that of methylmalonic acid (MMA). The spectral signal may be obtained using 2D COrelated SpectroscopY (2D COSY). The spectral signal may be obtained using data mining of a 1D MRS signal. The results may be compared to an International Breast cancer Intervention Study (IBIS) score of the subject.

The invention provides a system for enabling a determination of the risk of developing breast cancer of a subject, comprising: a processor for processing spectral data obtained from the breast tissue of the subject using a magnetic resonance spectroscopy device to obtain the level of the spectral signal at 3.15 and 3.19 ppm, and a comparator for comparing the level of the spectral signal obtained with a reference level of a spectral signal at 3.15 and 3.19 ppm from the breast of a healthy subject, to determine whether the level of the signal obtained exceeds the reference level of a healthy subject, is comparable to that of a subject known to be at elevated risk, or is elevated to the level of persons known to be carrying a gene mutation.

DESCRIPTION OF THE DRAWING FIGURES

Figures 1, 2:
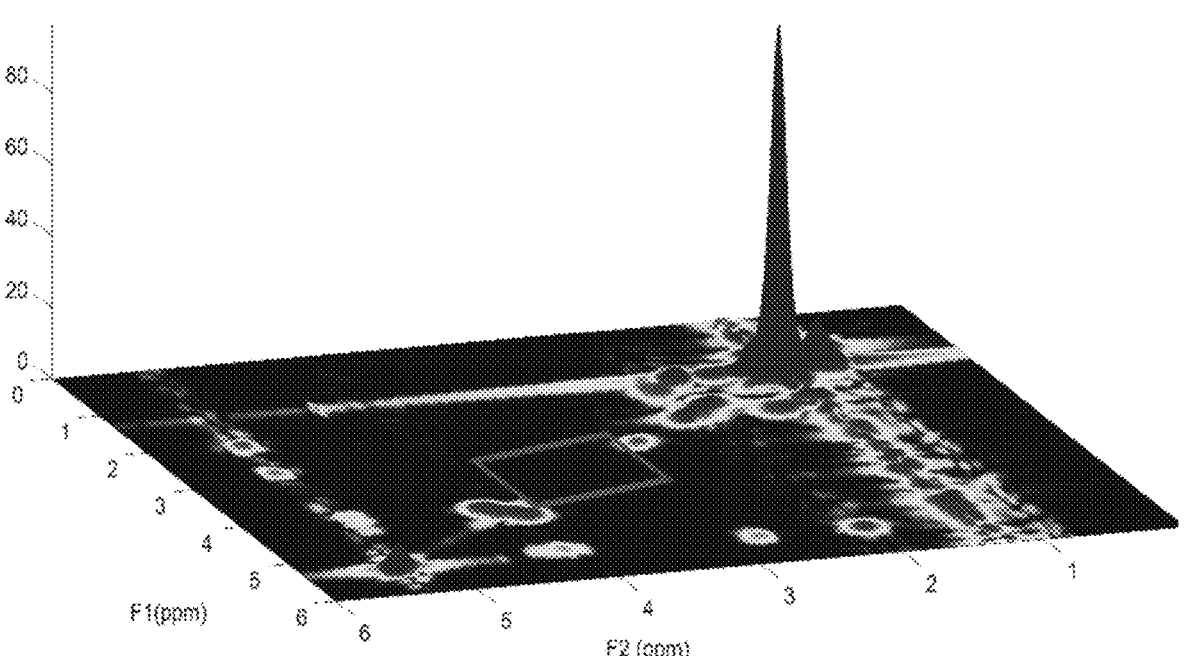
FIG. 1 shows the chemical structure of Methylmalonic acid (2-methylpropanedioic acid).
FIG. 2 shows a three-dimensional image of a 2D COSY breast spectrum from an apparently healthy premenopausal woman with a dense breast density of BIO-RADS 3. The area marked is the rectangular region shown in FIG. 3.
Figure 3:
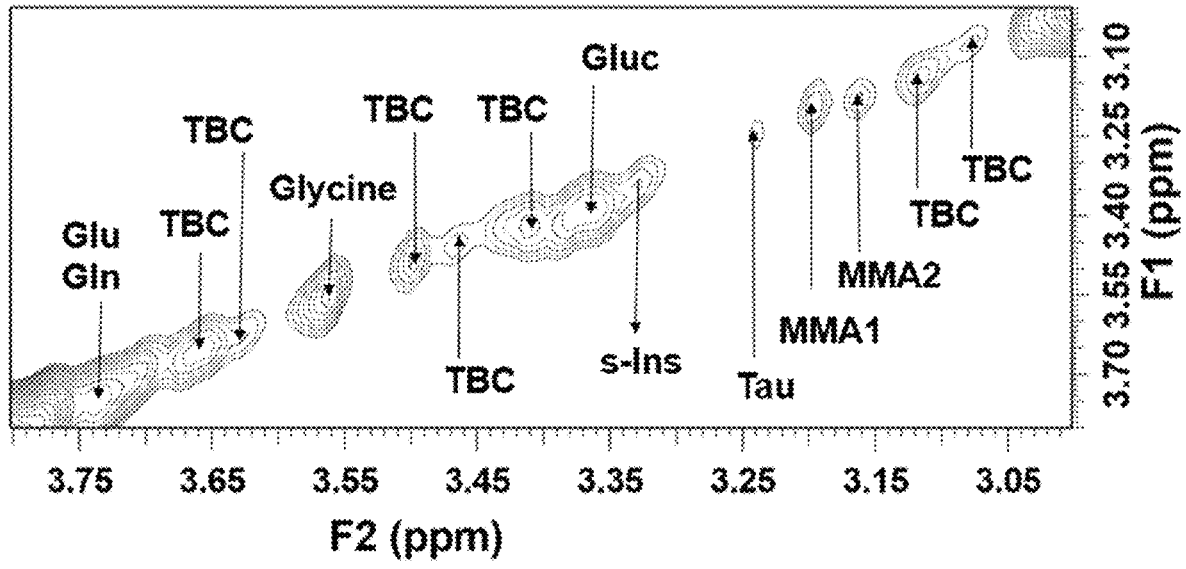

FIG. 3 shows a contour plot of the expanded region F2/F1 of FIG. 2.: 3.00 ppm to 3.90 ppm of a COSY recorded from a premenopausal woman with dense breast tissue, Contour plots demonstrate proton MR spectroscopy resonances, with tentative assignments for the MMA multiplet at 3.15 and 3.19 ppm, Other diagonal resonances are Gly: Glycerol; GPC: Glycerophosphocholine; Gly: Glycine; Glc: Glucose; Gln: Glutamine; Glu: Glutamate; His: Histidine; m-Ins: Myo-inositol; scyllo-Inositol; Tau: Taurine; Thr: Threonine; TBC: to be confirmed.

Figure 4:
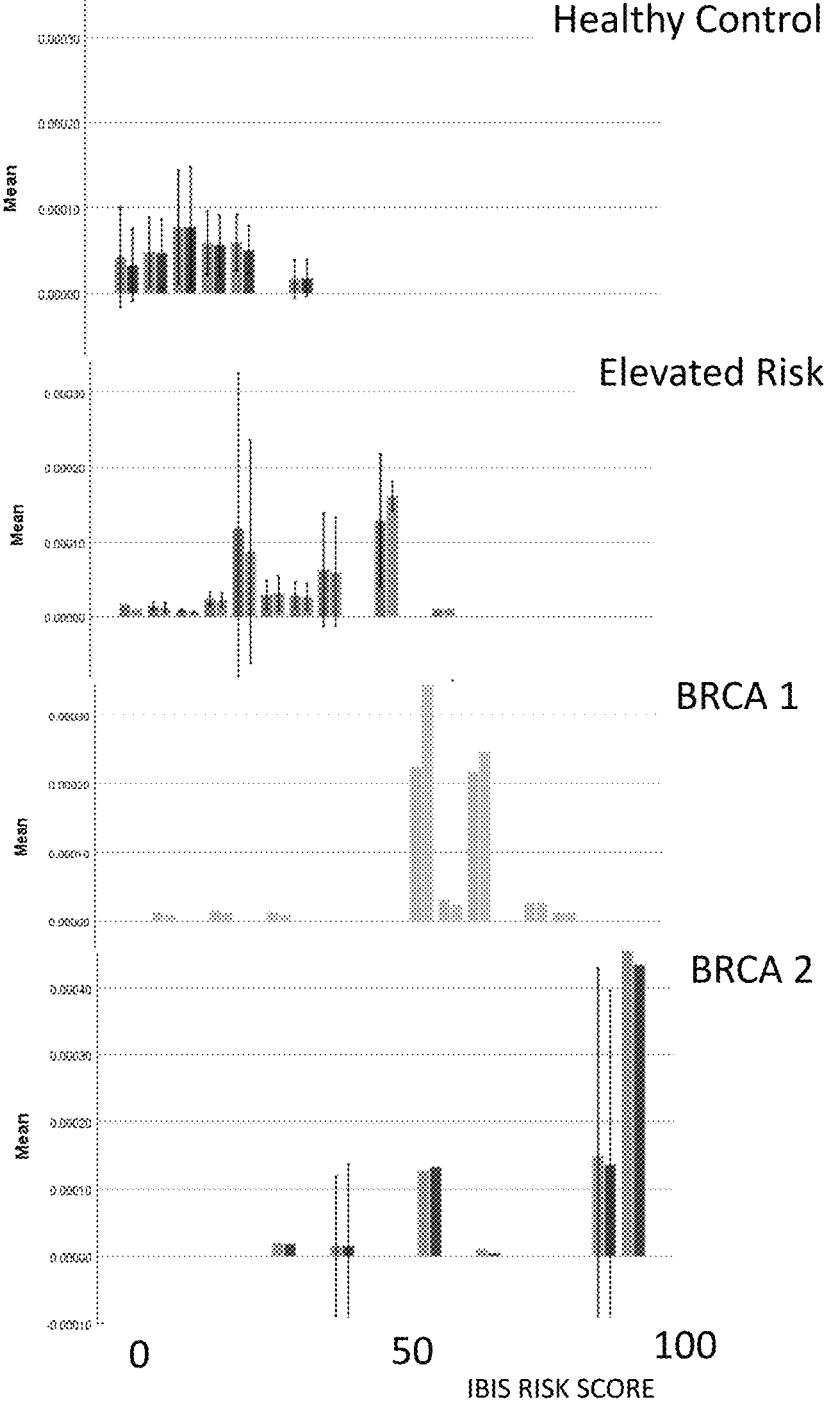

FIG. 4 shows the level of the resonances assigned to MMA at 3.15 and 3.19 ppm plotted against the IBIS score for each patient group. It can be seen that the respective levels of these MMA resonances are correlated to the IBIS score.

Figure 5:
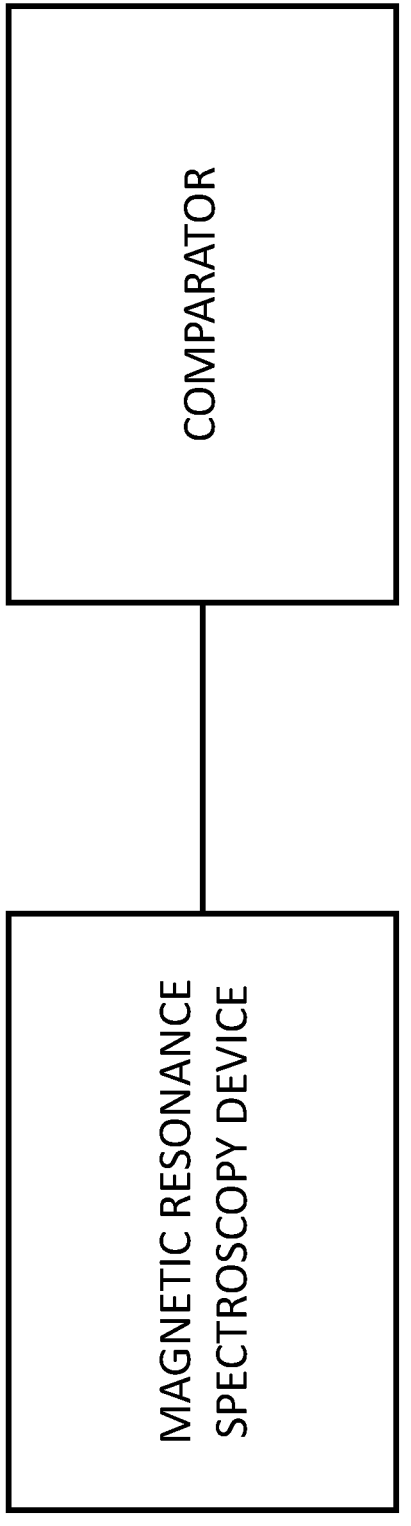

FIG. 5 shows a block diagram of a magnetic resonance spectroscopy device, and comparator.

DETAILED DESCRIPTION OF A PREFERRED EMBODIMENT

A preferred embodiment of the invention will be described, but the invention is not limited to this embodiment.

A 2D COSY from a woman with breast density of BI-RADS 3 is shown in FIG. 2. The lipid assignments are as described in Ramadan et al[8]. A contour plot of the expanded region F2/F1: 3.00 ppm to 3.90ppm is shown in FIG. 3 where resonances at 3.15 and 3.19 ppm are apparent and consistent with the presence of the MMA molecule. The second multiplet of MMA at 1.23 ppm is not visible due to the large methylene resonance from fatty acyl chains[2]. However, the crosspeak at 1.27-3.20 ppm showing scalar coupling of the methyl protons and methyne protons of MMA can also be recorded.

The intensity of these diagonal resonances was measured for all categories of women studied i.e. healthy women with no known risk for cancer; those at familial cancer risk; and those carrying the BRCA1 or BRCA2 gene mutation. All were evaluated for risk based on the IBIS score. These are shown in FIG. 3 where the level of the MMA recorded is directly correlated by the IBIS score.

The reason why women with dense breast tissue who are premenopausal have an elevated risk for breast cancer has remained a mystery and of concern. Breast density alone is not sufficient to render high risk for breast cancer. Here we tentatively assign resonances at 3.15 and 3.19 ppm to MMA. Other contenders for this assignment are tyrosine at 3.19 ppm and homocarnosine at 3.18 ppm but neither have the other resonances expected from that molecule in the spectra.

MMA, has recently reported to endow cancer cells with the properties necessary to migrate, invade, survive and thrive as metastatic lesions'. The report evaluates the aging population and suggests that MMA relies on the activation of TGFβ signaling in an autocrine fashion to induce SOX4 and consequently the transcriptional reprogramming necessary for the cellular plasticity that sustains tumor progression. If this assignment is correct, then this provides another piece in the puzzle as to why premenopausal women with dense breasts are at higher risk for breast cancer. Proof of assignment of these resonances can be made by chemical evaluation of breast tissue extractions to confirm the presence of MMA in the dense premenopausal breast tissue.

The capacity to non-invasively monitor breast tissue chemistry changes at a molecular level, using in vivo two-dimensional magnetic resonance spectroscopy, in an apparently healthy breast, shows great potential for the development of a personalised medicine approach. This is particularly relevant in the cohort of women with a family history that increases their lifetime risk of developing breast cancer, but without any other risk factor that places them in the group at greater than 20 percent lifetime risk.

This is the cohort in which the American Cancer Society does not recommend annual screening using dynamic contrast-enhanced MRI, but in which other modalities do not provide a sensitive or specific enough approach.

While the data were obtained using 2D COSY, it is possible that this information may be deduced using 1D MRS and data mining as developed for pain [9]. These resonances may be recorded and measured using a full 2D data set or a specific range of delays that encompass the strongest signal for the MMA. In conclusion, using in vivo MR spectroscopy two resonances can be searched for at 3.15 and 3.19 ppm in breast tissue. If the resonances are present, they are consistent with the presence of the MMA molecule in breast tissue. In healthy women, with no significant family history, those with highly dense breast tissue have five times higher levels of MMA than those with low breast density. In those women with an elevated risk of cancer, as judged by their IBIS score, the MMA is highest in those carrying the BRCA gene mutations. The amount of these two resonances, recorded at 3.15 and 3.19 ppm, increase linearly with the risk of breast cancer as deduced by the IBIS risk score. While the assignment of these resonances to MMA is only tentative at this stage, regardless of the exact assignment of the resonances, it appears that they correlate with lifetime risk of developing breast cancer, as measured using the IBIS score. Data mining of in vivo 1D MRS of breast tissue can be done to determine whether the MMA information can be extracted from a much shorter acquisition time in a scanner. In conclusion, using in vivo MR spectroscopy two resonances can be searched for at 3.15 and 3.19 ppm in breast tissue. If the resonances are present, they are consistent with the presence of the MMA molecule in breast tissue. In healthy women, with no significant family history, those with highly dense breast tissue have five times higher levels of MMA than those with low breast density. In those women with an elevated risk of cancer, as judged by their IBIS score, the MMA is highest in those carrying the BRCA gene mutations. The amount of these two resonances, recorded at 3.15 and 3.19 ppm, increase linearly with the risk of breast cancer as deduced by the IBIS risk score. While the assignment of these resonances to MMA is only tentative at this stage, regardless of the exact assignment of the resonances, it appears that they correlate with lifetime risk of developing breast cancer, as measured using the IBIS score. Datamining of in vivo 1D MRS of breast tissue can be done to determine whether the MMA information can be extracted from a much shorter acquisition time in a scanner.

REFERENCES (1) Gomes, A. P.; Ilter, D.; Low, V.; Endress, J. E.; Fernández-García, J.; Rosenzweig, A.; Schild, T.; Broekaert, D.; Ahmed, A.; Planque, M. et al. Age-induced accumulation of methylmalonic acid promotes tumour progression. *Nature* 2020, DOI:10.1038/s41586-020-2630-0 10.1038/s41586-020-2630-0.

(2) Commodari, F.; Arnold, D. L.; Sanctuary, B. C.; Shoubridge, E. A. J. N. i. b. 1H NMR characterization of normal human cerebrospinal fluid and the detection of methylmalonic acid in a vitamin B12 deficient patient. 1991, 4 (4), 192.

(3) Wishart, D. S.; Feunang, Y. D.; Marcu, A.; Guo, A. C.; Liang, K.; Vázquez-Fresno, R.; Sajed, T.; Johnson, D.; Li, C.; Karu, N. HMDB 4.0: the human metabolome database for 2018. *Nucleic acids research* 2018, 46 (D1), D608.

(4) McCormack, V. A.; dos Santos Silva, I. Breast Density and Parenchymal Patterns as Markers of Breast Cancer Risk: A Meta-analysis. *Cancer Epidemiology Biomarkers & Prevention* 2006, 15 (6), 1159.

(5) Boyd, N. F.; Lockwood, G. A.; Byng, J. W.; Tritchler, D. L.; Yaffe, M. J. Mammographic densities and breast cancer risk. *Cancer Epidemiol Biomarkers Prev* 1998, 7 (12), 1133.

(6) Duffy, S. W.; Morrish, O. W. E.; Allgood, P. C.; Black, R.; Gillan, M. G. C.; Willsher, P.; Cooke, J.; Duncan, K. A.; Michell, M. J.; Dobson, H. M.et al. Mammographic density and breast cancer risk in breast screening assessment cases and women with a family history of breast cancer. *European Journal of Cancer* 2018, 88, 48.

(7) Boyd, N. F.; Guo, H.; Martin, L. J.; Sun, L.; Stone, J.; Fishell, E.; Jong, R. A.; Hislop, G.; Chiarelli, A.; Minkin, S.et al. Mammographic density and the risk and detection of breast cancer. *N Engl J Med* 2007, 356 (3), 227.

(8) Ramadan, S.; Arm, J.; Silcock, J.; Santamaria, G.; Buck, J.; Roy, M.; Leong, K. M.; Lau, P.; Clark, D.; Malycha, P.et al. Lipid and Metabolite Deregulation in the Breast Tissue of Women Carrying BRCA1 and BRCA2 Genetic Mutations. *Radiology* 2015, 275 (3), 675.

(9) Stanwell, P.; Siddall, P.; Keshava, N.; Cocuzzo, D.; Ramadan, S.; Lin, A.; Herbert, D.; Craig, A.; Tran, Y.;

6

Middleton, J.et al. Neuro magnetic resonance spectroscopy using wavelet decomposition and statistical testing identifies biochemical changes in people with spinal cord injury and pain. *NeuroImage* 2010, 53 (2), 544.

The invention claimed is:

1. A method enabling a determination of a risk of developing breast cancer of a subject by in vivo acquisition of spectral data of a breast of the subject, comprising:
   a. using a magnetic resonance spectroscopy device to obtain a level of a spectral signal at 3.15 and 3.19 ppm (parts per million), within a breast tissue of the subject in vivo, and
   b. comparing (i) the level of the spectral signal obtained in step a. with (ii) a reference level of a spectral signal at 3.15 and 3.19 ppm from a breast of a healthy subject, to determine whether (i) the level of the signal obtained in step a. exceeds the reference level of a healthy subject from step b (ii); (ii) is comparable to that of a subject, known to be at elevated risk of developing breast cancer; or (iii) is elevated to the level of persons known to be carrying a gene mutation.

2. The method of claim 1, wherein the spectral signal obtained in step a is obtained using 2D (Two Dimensional) COrelated SpectroscopY (2D COSY).

3. The method of claim 1, wherein the spectral signal obtained in step a is obtained from a 1D (One Dimensional) MRS signal.

4. A system for enabling a determination of a risk of developing breast cancer of a subject by in vivo acquisition of spectral data of a breast tissue of the subject, comprising:
   a. a magnetic resonance spectroscopy device to obtain a level of a spectral signal at 3.15 and 3.19 ppm (parts per million), within a breast tissue of the subject, and
   b. a comparator for comparing (i) the level of the spectral signal obtained in step a. with (ii) a reference level of a spectral signal at 3.15 and 3.19 ppm from a breast of a healthy subject, to determine whether (i) the level of the signal obtained in step a. exceeds the reference level of a healthy subject from step b (ii), (ii) is comparable to that of a subject known to be at elevated risk, or (ii) is elevated to the level of persons known to be carrying a gene mutation.

5. The system of claim 4, wherein the spectral signal is obtained using 2D (Two Dimensional) COrelated SpectroscopY (2D COSY) or by using 1D (One Dimensional) MRS.

6. The system of claim 4, wherein the spectral signal obtained in step a is obtained using a 1D MRS signal.

7. A method enabling a determination of a risk of developing breast cancer of a subject, comprising:
   a. Processing spectral data obtained in vivo from a breast tissue of the subject using a magnetic resonance spectroscopy device to obtain a level of a spectral signal at 3.15 and 3.19 ppm (parts per million), and
   b. comparing (i) the level of the spectral signal obtained in step a. with (ii) a reference level of a spectral signal at 3.15 and 3.19 ppm from a breast of a healthy subject, to determine whether the level of the signal obtained in step a. (i) exceeds the reference level of a healthy subject from step b (ii); (ii) is comparable to that of a subject known to be at elevated risk; or (iii) is elevated to the level of persons known to be carrying a gene mutation.

8. The method of claim 7, wherein the spectral signal obtained in step a is obtained using 2D (Two Dimensional) COrelated Spectroscop Y (2D COSY).

9. The method of claim 7, wherein the spectral signal is obtained using a 1D (One Dimensional) MRS signal.

10. A system for enabling a determination of a risk of developing breast cancer of a subject by in vivo acquisition of spectral data of a breast tissue of a subject, comprising:

a. a processor for processing spectral data obtained in vivo from the breast tissue of the subject using a magnetic resonance spectroscopy device to obtain a level of a spectral signal at 3.15 and 3.19 ppm (parts per million), and b. a comparator for comparing (i) the level of the spectral signal obtained in step a. with (ii) a reference level of a spectral signal at 3.15 and 3.19 ppm from a breast tissue of a healthy subject, to determine whether the level of the signal obtained in step a. (i) exceeds the reference level of a healthy subject from step (b) (ii), (ii) is comparable to that of a subject known to be at elevated risk, or (iii) is elevated to the level of persons known to be carrying a gene mutation.

11. The system of claim 10, wherein the spectral signal obtained in step a is obtained using 2D (Two Dimensional) COrelated SpectroscopY (2D COSY) or by datamining 1D (One Dimensional) MRS.

12. The system of claim 10, wherein the spectral signal (obtained in step a) is obtained using data mining of a 1D MRS signal.

\*    \*    \*    \*    \*